United States Patent [19]

Kurie

[11] 4,270,317
[45] Jun. 2, 1981

[54] APPARATUS USED IN THE TREATMENT OF A CONTINUOUS STRIP OF METAL AND METHOD OF USE THEREOF

[75] Inventor: Eugene J. Kurie, Bridgewater, N.J.

[73] Assignee: Midland-Ross Corporation, Cleveland, Ohio

[21] Appl. No.: 126,937

[22] Filed: Mar. 4, 1980

Related U.S. Application Data

[63] Continuation of Ser. No. 949,872, Oct. 10, 1978, abandoned.

[51] Int. Cl.³ .......................... B24C 3/12; B24C 7/00
[52] U.S. Cl. ........................................ 51/426; 51/439; 51/321; 134/64 R
[58] Field of Search ................. 51/417, 426, 428, 439, 51/321, 7, 20; 134/15, 64, 122, 114, 199; 118/316

[56] References Cited

U.S. PATENT DOCUMENTS

| | | | |
|---|---|---|---|
| 2,489,097 | 11/1949 | Luce | 51/321 |
| 2,822,635 | 2/1958 | Mears | 134/64 X |
| 3,328,997 | 7/1967 | Beggs | 72/342 |
| 3,344,729 | 10/1967 | Kitrousser | 134/199 X |
| 3,358,980 | 12/1967 | Taylor | 134/122 R X |
| 3,502,563 | 3/1970 | Schmidt | 204/299 EC |
| 3,509,851 | 5/1970 | Barnes | 118/316 |
| 3,561,163 | 2/1971 | Arnold | 51/439 X |
| 3,682,185 | 8/1972 | Murray | 134/199 X |
| 3,687,145 | 8/1972 | Schrader | 134/114 |
| 3,734,109 | 5/1973 | Hebner | 134/64 R |
| 3,871,914 | 3/1975 | Goffredo | 134/199 X |
| 3,871,982 | 3/1975 | Idstein | 134/64 R X |
| 3,962,060 | 6/1976 | Brasko | 204/181 R |
| 4,162,955 | 7/1979 | Schregenberger | 118/314 X |

Primary Examiner—Gary L. Smith
Attorney, Agent, or Firm—Harlan E. Hummer

[57] ABSTRACT

An apparatus used in the treatment of a sheet of metal without the aid of conventional sprays and flooding nozzles normally used in the application of the metal treating liquid and support rollers and squeeze used for contacting and guiding the sheet of metal through successive baths of the metal treating liquid and preventing the carryover of liquid between the treatment tanks of the apparatus. In the apparatus, a sheet of metal is guided in a horizontal pathway between successive treatment tanks or units having horizontally elongated chambers with two rows of oppositely disposed and horizontally aligned nozzles between which the sheet of metal travels on a liquid bed that is created by the nozzles which are designed to direct streams of liquid, under pressure, against the traveling metal sheet at angles that are substantially less than 90° relative to the plane in which the metal sheet travels. A unique liquid seal and conventional blowoff device are utilized at each opening through which the traveling metal sheet enters and exits the various chambers, as a means of maintaining the liquid within the chamber and preventing it from being carried away by the traveling metal sheet into an adjacent chamber where the appearance of such liquid may have a deleterious affect upon the process being carried out in that particular chamber. The individual units are also free of brushes and other such devices which are normally used to aid in the cleaning of the sheet of metal.

27 Claims, 4 Drawing Figures

4,270,317

APPARATUS USED IN THE TREATMENT OF A CONTINUOUS STRIP OF METAL AND METHOD OF USE THEREOF

This is a continuation, of application Ser. No. 949,872, filed Oct. 10, 1978, now abandoned.

BACKGROUND OF THE INVENTION

The invention has a broad application in the treatment of a traveling web, but is especially useful in the treatment of a sheet of metal such as steel or aluminum. The term "treatment" as used herein and in the claims, has reference to any process where a continuous web, such as a sheet of metal, paper, film, or textile material, is contacted by a liquid or gas as it moves in a generally horizontal pathway through an enclosed chamber. For example, the treatment of a traveling web includes the electro-galvanizing, de-scaling, or pickling processes of metals, or the cleaning of the web by washing and rinsing, or any other suitable preparation of the web for any subsequent coating, drying saturating, or laminating of the web, or the subsequent operations themselves.

Systems presently on the market for cleaning a sheet of metal or otherwise preparing it for subsequent treatment, such as coating etc., normally employ squeeze rollers between the various treatment tanks for removing excess liquid from the traveling metal sheet so that liquid won't be carried from tank to tank to contaminate or dilute the various liquid solutions being used in the different tanks. However, these rollers become nicked, gouged and otherwise damaged by the sheet of metal to a point where they become ineffective in preventing the traveling metal sheet from carrying liquid between tanks. Such systems also use support rollers that are positioned within the tanks for contacting the traveling metal sheet and guiding it through the bath of liquid used in the treatment of the metal sheet. These support rollers are highly susceptible to rotating slower than the correlated linear speed at which the sheet of metal travels over the rollers to cause slippage between the rollers and sheet of metal and consequent marring of the surfaces of the sheet metal. Thus, the elimination of these two types of rollers would be highly beneficial in the treatment of a sheet of metal.

Sprays are generally used above and below the traveling metal sheet to direct liquid against the adjacent planar surfaces of the metal sheet. The liquid from the sprays contact the metal sheet at angles which are substantially 90° to the plane of the traveling metal sheet. It can be appreciated that the use of such sprays in conjunction with a horizontally traveling metal sheet, generally produces an uneven treatment of the upper and lower surfaces of the traveling metal sheet. For example, a liquid impinged against the top side or upper surface of the metal sheet can form into pools or puddles of liquid which interfere with the impingement upon the surface of liquid from succeeding sprays. In essence, the top side of the metal sheet is usually subjected to a bath or soak process. The opposite is true regarding the processing of the bottom side or lower surface of the traveling metal sheet, where gravity causes the immediate withdrawal of the liquid directed against the bottom side by the sprays located below the traveling metal sheet. In essence, the bottom side of the metal sheet is usually subjected to a spray and drip process. Thus, the opposing surfaces of the traveling metal sheet are exposed to different processing conditions which usually produces non-uniform treatment of the opposing surfaces of the traveling metal sheet.

U.S. Pat. No. 3,328,997 discloses the use of floatation-type nozzles for impinging cleaning liquid against a traveling web. However, the particular apparatus of this patent utilizes in the liquid bath, a number of support rollers which, as previously indicated, can have a deleterious affect upon the treatment of the metal within the bath. The invention is directed to an improved apparatus for the treatment of a traveling web in a liquid bath.

Briefly stated, the invention is in an apparatus used in the treatment of a continuous web or element, such as a sheet of metal, at it travels in a horizontal pathway. The apparatus comprises at least one tank having a horizontally elongated chamber with opposing end walls having horizontally aligned openings through which the traveling metal sheet enters and exits the chamber. Two rows of oppositely disposed, horizontally aligned elongated nozzles, normal to the direction of travel of the metal sheet, are provided in the chamber and positioned to sandwich the traveling metal sheet therebetween. At least one longitudinally extending continuous slot, coextensive with the lateral width of the metal sheet, is provided in the face of each nozzle confronting the traveling metal sheet, and a deflector is provided on each nozzle adjacent the slot for directing a turbulent stream of liquid from the slot angularly against the traveling metal sheet in a direction which is upstream or opposite the direction in which the sheet of metal travels.

A unique liquid seal in the form of a pair of oppositely disposed, similar liquid nozzles, is utilized at the entrance and exit openings of the chamber in combination with air blowoff devices for sealing the openings to prevent the escape of liquid from the chamber into the chamber of an adjacent tank where such liquid could have a harmful affect upon the process being carried on in that particular tank.

Another aspect of the invention is the provision between adjacent nozzles in the chamber of a turbulator which is simply a nozzle that directs a high pressure jet of liquid directly against the traveling metal sheet at an angle of substantially 90°, to clash with the highly turbulent flow of liquid produced by the nozzles and create even greater turbulence adjacent the surfaces of the traveling metal sheet.

The successive streams of liquid, as they angularly contact the metal sheet in a counter direction at angles substantially less than 90°, provides a unique scrubbing action that is normally not accomplished by the sprays of prior art devices and eliminates the need for auxiliary cleaning equipment, such as scrubbing brushes and other like paraphernalia. The result is an improvement in the quality of the treatment of the metal sheet and consequent reduction in the time required to properly treat the metal sheet.

The liquid seals and blowoff devices eliminate the need for squeeze rollers between adjacent treatment tanks and effectively control the carryover of liquid between adjacent tanks normally experienced when the squeeze rollers become nicked, gouged, or otherwise damaged beyond repair. Consequent contamination or dilution of the liquid of the various treatment tanks is minimized to eliminate the need for frequent replenishment of the liquid and periodic discharge from the tanks of the tainted or weakened liquid which can cause pollution of the drainage system in which such liquid is wasted.

Moreover, the need for guide rollers within the tanks is eliminated because of the liquid beds which are created within the tanks to support the metal sheet. Thus, many of the problems experienced with prior art devices are eliminated, or substantially reduced to where they are inconsequential.

DESCRIPTION OF THE DRAWING

The following description of the invention will be better understood by having reference to the accompanying drawing, wherein.

DESCRIPTION OF THE INVENTION

Figure 1:
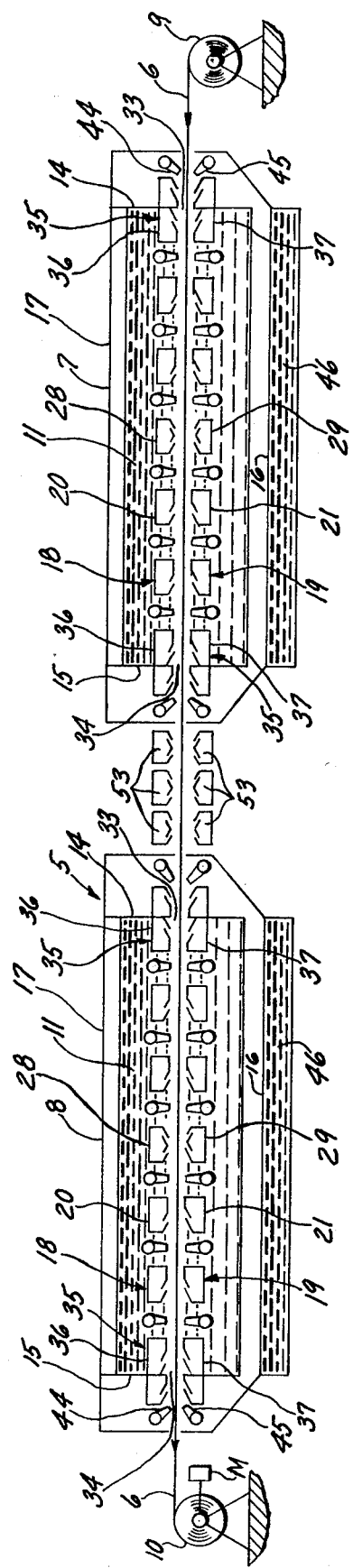
FIG. 1 is a section taken longitudinally of two cleaning units or tanks which are made in accordance with the invention and schematically shown, in tandem.
Figure 2:
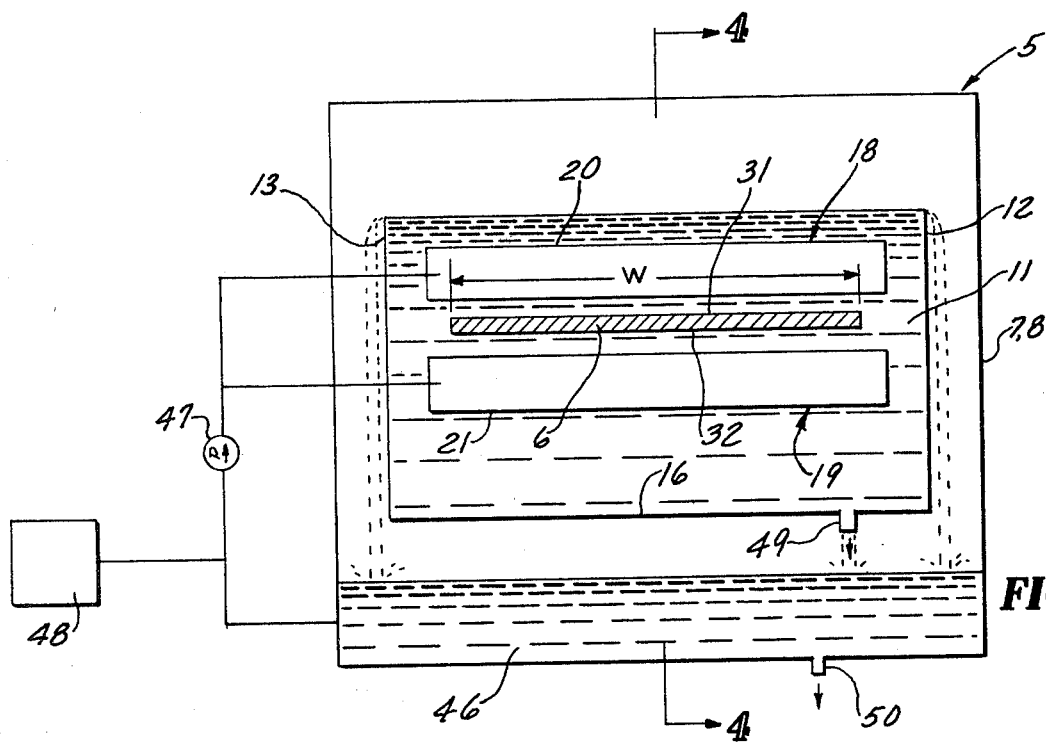
FIG. 2 is a section of one of the cleaning units, as viewed from the line 2—2 of FIG. 1, certain controls of the unit being schematically shown.
Figure 4:
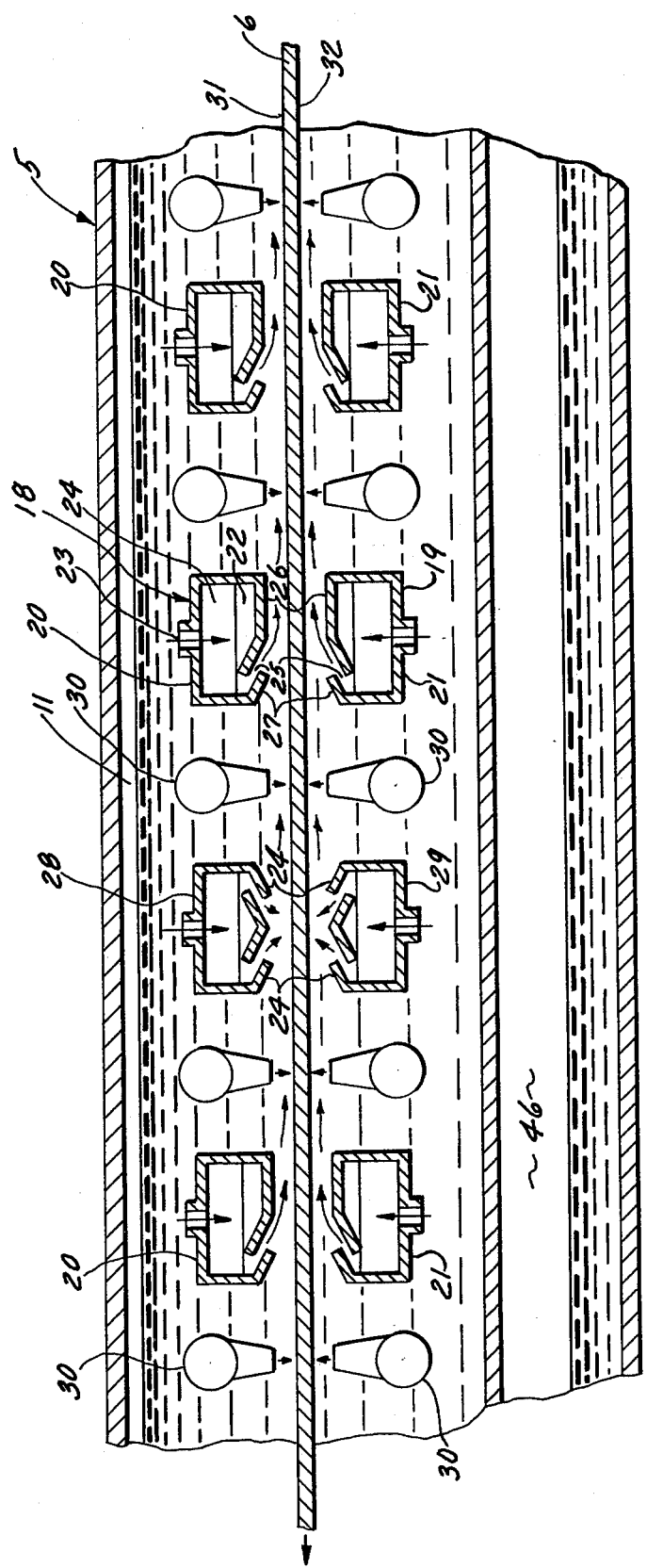
FIG. 4 is a section of a portion of the cleaning unit of FIG. 1, as viewed from the line 4—4 of FIG. 2.

With reference to FIGS. 1, 2 and 4, there is shown an apparatus 5 used in the treatment, e.g. cleaning, of a traveling web such as a sheet 6 of metal, e.g. steel or aluminum. The apparatus 5, in this instance, comprises at least two adjacently disposed tanks 7,8 in which the traveling metal sheet 6 is washed and rinsed, respectively. The metal sheet 6 is removed from a conventional leftoff 9 and transported in a substantially horizontal pathway successively through the wash tank 7 and rinse tank 8 from which the metal sheet 6 is removed onto a conventional windup or coiling device 10 which is driven or rotated by any suitable drive mechanism M.

The tanks 7,8 each have a horizontally elongated, rectangularly shaped chamber 11 which is bounded by longitudinally extending sidewalls 12,13, opposing endwalls 14,15, and bottom 16. The chambers 11 are each centrally disposed within, and spaced from, the outer surrounding walls or shell 17 of each of the tanks 7,8. The chambers 11 of adjacent tanks 7,8 are spaced from each other and disposed end to end or, in tandem.

Two rows 18,19 of oppositely disposed horizontally aligned similar, elongated floatation-type treatment nozzles 20,21 are disposed in each of the chambers 11 and positioned to sandwich the traveling metal sheet 6 therebetween, the rows 18,19 of nozzles 20,21 of adjacent tanks 7,8 being likewise horizontally aligned to maintain the traveling metal sheet 6 in a substantially horizontal pathway through both of the tanks 7,8.

The treatment nozzles 20,21, as best seen in FIGS. 1, 2 and 4, are parallel and normal to the direction in which the metal sheet 6 travels, and are at least coextensive with the lateral width W of the metal sheet 6. The nozzles 20,21 are similar in design and, as best seen in FIG. 4, are each comprised of an enclosed compartment 22, an inlet 23, through which liquid enters the compartment 22, a baffle 24 for uniform distributing of the liquid to a continuous slot 25 which is disposed in the surface or face 26 of the nozzles 20,21 confronting the traveling metal sheet 6, and a deflector 27 which is disposed adjacent the slot 25 to direct a steady turbulent stream of liquid, under pressure, from the slot 25 angularly against the traveling metal sheet 6 in a direction which is upstream or opposite the direction in which the metal sheet 6 travels past the nozzles 20,21. Successive streams of cleaning or rinsing liquid, under pressure, are directed from the nozzles 20,21 against the traveling metal sheet 6 at angles which are substantially less than 90° relative to the plane of the traveling metal sheet 6, i.e. at angles less than 45° and preferably in the range of from 10°-30°. Occasionally, a pair of opposing nozzles 28,29 (FIG. 4) may be provided with two parallel continuous slots and deflectors for directing two angularly opposed, intersecting streams of liquid against the metal sheet 6 to help stabilize movement of the metal sheet 6 in the horizontal pathway but, in most cases, it is more desireable to direct the streams of liquid in the same directions against the traveling metal strip 6 to form a highly turbulent flow of liquid adjacent and parallel the metal sheet 6 in an upstream or counter-flow direction.

Further agitation or turbulence for increased cleaning action can be provided by positioning a turbulator 30 between each pair of adjacent treatment nozzles 20 or 21. A turbulator 30 is simply an ordinary high pressure/low volume single outlet nozzle which extends transversely of the metal sheet 6 and is designed to direct a jet of liquid, under pressure, directly and not angularly against the traveling metal sheet 6, i.e. at an angle which is substantially 90° to the plane of the traveling metal sheet 6. The jets of liquid from the turbulators 30 break up or clash with the steady, turbulent flow of liquid from the treatment nozzles 20,21 to create even greater turbulence adjacent the traveling metal sheet 6.

Still further cleaning action can be provided by employing an abrasive cleaning material, such as silica, sand, or talcum, in the cleaning liquid which is circulated through the treatment nozzles 20,21 and turbulators 30. The use of such abrasive cleaning solutions eliminates the need for brush scrubbers which are normally used in the early cleaning stages for removing rust and scale from a metal sheet 6 and reduces the time generally required for properly treating the metal sheet 6. Because of the abrasive character of such material, it is best to construct the treatment nozzles 20,21, turbulators 30 and any other nozzles through which the abrasive cleaning solution is circulated, of a durable, wear-resistant material which is compatible with the solution. For example, ordinary steel nozzles can be lined with rubber, plastic, or any other appropriate material which is unaffected by the abrasiveness of the cleaning solution. The aforementioned nozzles should be composed of any suitable, durable and liquid resistant material when, for example, highly corrosive chemicals, acids, or harmful detergents are employed as a liquid in the treatment of the traveling web.

The tanks 7,8 are filled with liquid to a level where the treatment nozzles 20,21 and turbulators 30 are preferably submerged in the liquid bath in each of the chambers 11, although in certain types of treatment of the metal sheet 6, it may be more beneficial to maintain the level of the liquid below the vertically lowermost row 19 of treatment nozzles 21. The treatment nozzles 20,21 and turbulators 30 are positioned sufficiently close to the traveling metal sheet 6 to provide a good scrubbing and cleaning of the metal even though they may be completely submerged in the liquid bath. The streams of liquid from the treatment nozzles 20,21 are utilized for a two-fold purpose; namely, they provide a turbulent scrubbing action of the liquid against the adjacent opposing upper and lower surfaces 31,32 of the traveling metal sheet 6, and they form a liquid bed on which the sheet 6 of metal is supported as it travels through the treatment chambers 11 of the two tanks 7,8.

Figure 3:
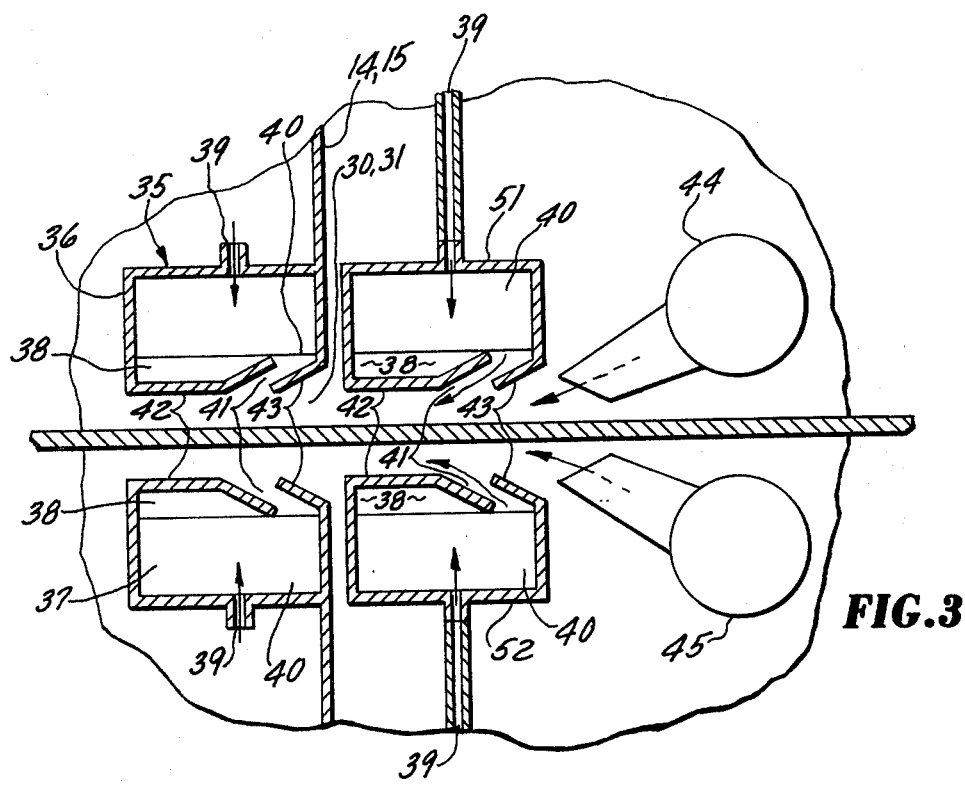
FIG. 3 is an enlarged section of the liquid seal and blowoff device for sealing the openings through which a traveling web enters and exits the chamber of each of the units.

The end walls 14,15 of each of the chambers 11 are provided with horizontally and laterally elongated openings 33,34 that are horizontally aligned and through which the traveling metal sheet 6 enters and exits the chambers 11. A unique liquid seal 35, as disclosed in copending application Ser. No. 949,873 filed Oct. 10, 1978 and best seen in FIG. 3, is provided for sealing each one of the openings 33,34 around the metal sheet 6 to prevent the escape of liquid from the tanks 6,7 through the openings 33,34. Conventional flap seals are inadequate, since the traveling metal sheet 6, especially the ragged spliced ends and edges of two overlapped sheets of metal, tears and eventually destroys them, thereby necessitating a complete shutdown of the process to replace the flap seals with new ones to prevent the mass escape of liquid from the tanks 7,8.

The liquid seals 35 each comprise a pair of parallel, oppositely disposed elongated sealing nozzles 36,37 which are similar in design to the treatment nozzles 20,21 used in the washing and rinsing of the traveling metal strip 6. The sealing nozzles 36,37 are likewise positioned crosswise of the traveling metal sheet 6 and sandwich the traveling metal sheet 6 therebetween adjacent the openings 33,34. The sealing nozzles 36,37, each have a longitudinally extending compartment 38 with an inlet 39 and conventional baffling 40 for uniformly distributing liquid, under pressure, from the compartment 38 through a continuous slot 41 disposed in the sheet confronting surface or face 42 of the nozzles 36,37. A deflector 43 is adjacent each slot 41 for directing a continuous stream of liquid, under pressure, angularly against the traveling metal strip 6 in the direction of the chambers 11. The streams of liquid from opposing pairs of sealing nozzles 36,37, converge toward the traveling metal sheet 6 in the direction of the chambers 11 to form adjacent and parallel the surfaces 31,32 of the traveling metal sheet 6, a turbulent back flow of liquid into the chambers 11. The steady flow of liquid from the sealing nozzles 36,37 is of sufficient mass and velocity to block the liquid attempting to escape the chambers 11 through the openings 33,34 and to provide a liquid bed for supporting the traveling metal sheet 6 adjacent the end walls 14,15 of the chambers 11. Thus, the liquid seals 35 serve a two-fold purpose and are especially designed to prevent the carryover of liquid between adjacent treatment tanks which utilize different liquids whose mixture is undesireable.

A pair of conventional blowoff nozzless 44,45 are provided outside and adjacent each of the openings 33,34 of the end walls 14,15 in further spaced relation from the chambers 11 and, like the sealing nozzles 36,37 of the liquid seals 35, direct streams of air, under pressure, angularly against the traveling metal sheet 6 at angles substantially less than 90° to the plane of the traveling metal sheet 6 and in the direction of the chambers 11 to help prevent the escape of liquid from the chambers 11 and to provide a cushion of air to aid in the support of the traveling metal sheet 6 adjacent the end walls 14,15. Any suitable blower or fan may be used to circulate air through the blowoff nozzles 44,45. The liquid which is blown off the traveling metal sheet 6 and captured during the attempted escape is, as best seen in FIG. 1, returned, by gravity, to a reserve or storage compartment 46 which is disposed in the lowermost portion of each of the tanks 7,8 and from which the captured liquid can be recirculated to the treatment nozzles 20,21, sealing nozzles 36,37 and turbulators 30 by a conventional pump 47 (FIG. 2) which can also be used to continuously circulate fresh, unused liquid from a source of supply 48 to the compartment 46 or the chambers 11 via the nozzles 20,21,36, 37 and turbulators 30 even after the treatment nozzles 20,21 and turbulators 30 are submerged and the liquid overflows the chambers 11 into the lower storage compartments 46. In this manner, liquid used in the treatment of the metal sheet 6 is continuously circulated between the treatment chambers 11 and storage compartments 46. Drains 49,50 are provided in each of the chambers 11 and lower compartments 46 to drain liquid from the tanks 7,8. Circulation of liquid between the chambers 11 and storage compartments of each of the tanks 7,8 can also be maintained by sizing the drain 41 of the upper chamber 11 so that there will be a constant flow of liquid between the chambers 11 and storage compartments 46 when the drain 49 is left open.

The liquid seals 35 and blowoff nozzles 44,45 effectively control the undesireable circulation of liquid between the tanks 7,8 and eliminates the need for conventional squeeze rollers that are normally used when ordinary flap seals are employed to seal the entrance and exit openings of the tanks 7,8. In some instances, it may be desireable to provide additional blowoff devices, since the blowoff nozzles 44,45 are designed to supply a comparatively low volume of air at relatively high pressures. If so, a second pair of air floatation-type nozzles 51,52 can be positioned between each of the liquid seals 35 and the adjacent high pressure blowoff nozzles 44,45. The floatation-type nozzles 51,52 are designed to supply a comparatively high volume of air at relatively low pressures and, as best seen in FIG. 3, are similar in structural design to the liquid sealing nozzles 36,37 of the liquid seals 35. The use of the floatation-type nozzles 51,52 in combination with the high pressure blowoff nozzles 44,45 can provide considerable savings in energy because the bulk of any liquid escaping through the liquid seals 35 can be removed from the metal sheet 6 by the greater mass of air flowing from the low pressure/high volume floatation-type nozzles 51,52 which require less energy to operate continuously than the high pressure/low volume blowoff nozzles 44,45.

Because of their effectiveness, the liquid seals 35, alone or in combination with the blowoff nozzles 44,45, and/or air floatation nozzles 51,52, can also be employed in place of the squeeze rollers of customary treatment tanks that rely on conventional sprays or flooding nozzles for applying liquid to a traveling web. A plurality of air floatation-type nozzles 53 with one or two continuous slots, or with intermittently spaced slots with rectangular or eyelid-shaped deflectors, can be provided between adjacent tanks 7,8 to create a cushion of air or other appropriate fluid bed for supporting the traveling metal sheet 6 between the tanks 7,8, if spaced any appreciable distance apart.

It can be appreciated that other tanks or units, such as a dryer can be place, in tandem, with the rinse tank 8, and similar floatation nozzles used therein to heat and dry the traveling metal sheet 6. Moreover, other similar tanks or units can be used to successively coat, bake and cool a liquid coating on the traveling metal sheet 6, after it has been properly cleaned and prepared to receive such subsequent treatment, prior to coiling on the windup device 10.

Thus, there has been described an apparatus which is free of rollers and provides successive streams of liquid, under pressure, to contact a traveling web at comparatively low angles relative to the plane of the web and in a direction opposite that in which the web travels. The apparatus is especially useful in the cleaning of a sheet of metal, prior to its being coated with a protective film such as paint. The particular floatation nozzles used in the successive tanks act not only to support the traveling metal sheet on a bed of liquid used in the treatment of the metal sheet, but also direct such liquid against the traveling metal sheet in such a way as to provide a thorough scrubbing of the adjacent surfaces of the sheet of metal. It can be appreciated that the cleaning action on both surfaces of the traveling metal sheet is substantially the same, especially when the treatment nozzles are submerged, to consequently provide more uniform processing of the surfaces.

What is claimed is:

1. An apparatus used in the treatment of a traveling web, comprising:
   (a) a tank having a horizontally elongated chamber enclosed therein, the chamber being free of any rollers for contacting the web traveling therethrough and having a pair of opposing end walls having therein, openings which are horizontally aligned and elongated and through which the traveling web enters and exits the chamber in a horizontal pathway;
   (b) means for supporting the web on turbulent streams of liquid as the web travels through the chamber, including two parallel rows of treatment nozzles extending longitudinally of and within the chamber and positioned to sandwich the traveling web therebetween, each row of nozzles including a number of transversely oriented elongated nozzles relative to the direction of travel of the web through the chamber, at least a majority of the nozzles each having:
      (I) a longitudinally extending compartment with an inlet therein;
      (II) a single continuous slot disposed in the surface of the nozzle confronting the traveling web, the slot being in communication with the compartment and extending transversely across the web;
      (III) a deflector adjacent the slot for directing a continuous stream of liquid, under pressure, from the slot angularly against the traveling web at an angle substantially less than 90° to the plane of the web;
   (bb) means for circulating liquid, under pressure, through the nozzles which coact with the liquid circulating means to impinge turbulent streams of liquid against the traveling web; and
   (c) a liquid seal disposed adjacent each of the openings in the end walls of the chamber for preventing the escape of liquid from the chamber, each of the seals including a pair of oppositely disposed sealing nozzles sandwiching the traveling web therebetween, the sealing nozzles having slots and deflectors designed to direct converging streams of liquid, under pressure, angularly against the traveling web at angles substantially less than 90° to the plane of the web in the direction of the chamber.

2. The apparatus of claim 1, which includes:
   (d) a pair of blowoff nozzles disposed adjacent each of the liquid seals and spaced a distance from the chamber farther than the seals and sandwiching the traveling web therebetween, each pair of blowoff nozzles designed to direct converging streams of air, under pressure, angularly against the traveling web at angles substantially less than 90° to the plane of the web and in the direction of the adjacent seal and chamber, to prevent the escape of liquid from the tank and aid in the support of the traveling web adjacent the end walls of the chamber.

3. The apparatus of claim 2, which includes a storage compartment disposed vertically below the chamber, and means for discharging to the storage compartment, liquid removed from the traveling web by air from the blowoff nozzles.

4. The apparatus of claim 3, which includes means coacting with the chamber for removing liquid overflowing the chamber to the storage compartment.

5. The apparatus of claim 4, wherein the streams of liquid are directed against the traveling web at angles less than 45° relative to the plane of the web.

6. The apparatus of claim 5, wherein liquid in the chamber is maintained at a level where the treatment nozzles are submerged therein.

7. The apparatus of claim 6, which includes:
   (e) a turbulator disposed between adjacent nozzles of each row of treatment nozzles for directing a jet of liquid, under pressure, at substantially right angles against the traveling web break up the turbulent flow of liquid coacted by the treatment nozzles along the traveling web.

8. An apparatus used in the treatment of a continuous web, comprising:
   (a) at least two adjacently disposed tanks with horizontally spaced and elongated chambers through which the continuous web successively travels for treatment in a horizontal pathway free of rollers normally used to engage and guide the web as it travels through the chambers;
   (b) means for supporting the web on turbulent streams of liquid as the web travels through the chambers of the two tanks, including two vertically spaced rows of treatment nozzles disposed in each of the chambers and extending longitudinally thereof in the direction which the web travels through the chambers, the rows of nozzles in adjacent chambers being substantially horizontally aligned and positioned to sandwich the web therebetween as it travels in the horizontal pathway, each of the nozzles extending transversely of the direction in which the web travels and having at least one continuous slot which faces the traveling web and extends transversely thereacross;
   (c) means for circulating liquid, used in the treatment of the traveling web, into the nozzles and uniformly out the slots thereof in the direction of the traveling web, the nozzles and liquid circulating means coacting to impinge turbulent streams of liquid against the traveling web; and
   (d) a deflector adjacent each of the slots and coextensive therewith for directing liquid, under pressure, from the nozzles against the traveling web at an angle which is substantially less than 90° relative to the plane of the traveling web and in a direction which is upstream and opposite the direction which the web travels past the nozzles.

9. The apparatus of claim 8, which includes:
  (e) a turbulator disposed between adjacent nozzles of each row of nozzles for directing a jet of liquid, under pressure, at substantially right angles against the traveling web to breakup the turbulent flow of liquid from the nozzles along the traveling web.

10. The apparatus of claim 8, which includes means for stabilizing movement of the web as it travels through the chambers, including at least one pair of opposing nozzles each of which is provided with (i) a pair of parallel, longitudinally extending continuous slots, and (ii) a pair of deflectors adjacent the slots and converging in the direction of the traveling web.

11. The apparatus of claim 8, wherein the chambers each have a pair of opposing end walls with horizontally aligned openings through which the traveling web enters and exits the chambers in a horizontal pathway, and a liquid seal disposed adjacent each of the openings for preventing the escape of liquid through the openings, each of the liquid seals including:
  (I) a pair of sealing nozzles adjacent each of the openings and positioned to sandwich the traveling web therebetween as it travels through the opening, the pair of sealing nozzles being coextensive with the opening and having confronting faces in which continuous slots are disposed longitudinally of the sealing nozzle and coextensive with an adjacent opening; and
  (II) a pair of deflectors adjacent the slots of each pair of sealing nozzles and converging in the direction of the traveling web and chambers to direct continuous streams of liquid, under pressure, angularly against the traveling web and liquid attempting to escape at angles substantially less than 90° to the plane of the web.

12. The apparatus of claim 11, which includes a pair of blowoff nozzles disposed adjacent each of the liquid seals in farther spaced relation from the chambers than the seals and sandwiching the traveling web therebetween, each of the blowoff nozzles traversing the traveling web and having at least one continuous slot facing the traveling web for directing a continuous stream of air, under pressure, angularly against the traveling web in the direction of the seals and chambers to aid in the support of the traveling web and to help prevent the escape of liquid from the tanks.

13. The apparatus of claim 8, wherein the liquid in the chambers is maintained at a level where the treatment nozzles are submerged.

14. The apparatus of claim 8, which includes an abrasive material in the liquid for treating the traveling web.

15. The apparatus of claim 14, wherein the abrasive material is from the group of silica, sand and talcum.

16. An apparatus used in the treatment of a traveling web, comprising:
  (a) at least two separate adjacently disposed tanks with horizontally elongated treatment chambers in spaced end-to-end relation through which a continuous web successively travels in a substantially horizontal pathway, each of the chambers being free of any rollers for contacting the web and including opposing end walls with horizontally aligned and elongated openings through which a traveling web enters and exits the chamber;
  (b) means for supporting the web on turbulent streams of liquid as the web travels through the chambers of the two tanks, including two vertically spaced rows of elongated treatment nozzles in each of the chambers and positioned for sandwiching the traveling web therebetween, the rows of treatment nozzles of the adjacent chambers being substantially horizontally aligned, the treatment nozzles having parallel longitudinal axes which are normal to the direction which the web travels past the nozzles, each of the treatment nozzles including:
    (I) longitudinally extending compartment having an inlet;
    (II) at least one continuous slot communicating with the compartment and confronting the traveling web, the slot extending transversely across the web; and
    (III) means for uniformly distributing the liquid to the slot from the inlet;
    (IV) a deflector disposed adjacent the slot and coextensive therewith and angularly disposed to a plane which contains a longitudinal axis of the nozzle and is normal to the plane of the nozzle, for directing liquid from the nozzle angularly against the traveling web at an angle which is substantially less than 90° to the plane of the traveling web and in a direction upstream and opposite the direction which the web travels past the nozzle;
  (c) means for circulating a liquid, used in the treatment of the traveling web, through the nozzles in each chamber, the nozzles and liquid circulating means coacting to impinge turbulent streams of liquid against the traveling web;
  (d) a turbulator between each pair of adjacent nozzles of each row of nozzles for directing a jet of liquid, used in the treatment of the traveling web, under pressure, directly against the traveling web at right angles thereto to cause more turbulent flow of liquid along the traveling web;
  (e) a liquid seal disposed adjacent each of the openings in the end walls of the chamber to prevent the escape of liquid through the openings, each of the liquid seals including:
    (I) a pair of confronting sealing nozzles sandwiching the traveling web therebetween and having continuous longitudinally extending slots facing the traveling web and through which liquid passes, under pressure, from the sealing nozzles;
    (II) deflectors disposed adjacent the slots of the confronting sealing nozzles and converging in the direction of the traveling web and adjacent chamber for directing continuous streams of liquid angularly against the traveling web in the direction of the adjacent chamber in sufficient mass and velocity to block the escape of liquid through the openings; and
  (f) a pair of confronting blowoff nozzles spaced from the chambers beyond each of the liquid seals and sandwiching the traveling web therebetween, said confronting pairs of blowoff nozzles likewise having continuous openings which face the traveling web and through which streams of air, under pressure, are directed angularly against the traveling web in the direction of the seals and chambers to aid in the support of the traveling web and help prevent the escape of liquid from the tanks.

17. The apparatus of claim 16, wherein liquid in the chambers is maintained at a level where the treatment nozzles and turbulators are submerged.

18. The apparatus of claim 17, which includes in at least one of the chambers, at least one pair of confronting treatment nozzles each of which has a pair of parallel slots and a pair of deflectors adjacent the slots and converging in the direction of the traveling web to direct intersecting streams of liquid, under pressure, angularly against the traveling web to help stabilize its movement in the chamber.

19. The apparatus of claim 18, which includes an abrasive material in the liquid being circulated through the treatment nozzles in at least one of the chambers.

20. The apparatus of claim 19, wherein each of the treatment nozzles is lined with elastomeric wear-resistant material compatible with the abrasive material to protect the nozzle from the abrasiveness of the material.

21. A method of treating a traveling web, in a chamber comprising:
  (a) moving the web through the chamber along a substantially horizontal pathway free of contact with any rollers in the chamber, the traveling web entering and exiting the chamber through openings in end walls of the chamber;
  (b) contacting opposing planar surfaces of the traveling web in the chamber intermediate the openings with successive turbulent streams of liquid, under pressure, to treat the traveling web while supporting it on a liquid bed formed by said streams which contact the traveling web at angles substantially less than 90° to the plane of the web and in directions which are upstream and opposite the direction in which the web travels; and
  (c) contacting the opposing planar surfaces of the traveling web adjacent each of the openings with two turbulent streams of liquid, under pressure, which converge upon the web at angles substantially less than 90° thereto and in the direction of the chamber to prevent the escape of liquid from the chamber through the openings.

22. The method of claim 21, which includes:
  (d) contacting the opposing planar surfaces of the traveling web outside the chamber and beyond each of the openings in the end walls, with at least two streams of air, under pressure, which converge towards the traveling web at angles substantially less than 90° thereto and in the direction of the chamber to help prevent the escape of liquid.

23. The method of claim 22, which includes:
  (e) contacting the opposing planar surfaces of the traveling web directly with jets of liquid, under pressure, between said successive streams of liquid, at angles of substantially 90° to the plane of the web.

24. The method of claim 23, which includes contacting opposing planar surfaces of the traveling web with a liquid that contains abrasive material for helping clean the web.

25. The method of claim 24, which includes:
  (f) moving the web successively through at least two separate horizontally elongated chambers in end-to-end spaced relation along a substantially horizontal pathway between two horizontally aligned rows of treatment nozzles in each of the chambers free of any contact with any support rollers in and between said chambers.

26. The method of claim 23, which includes submerging the traveling web in an identical liquid while contacting the web with successive streams of liquid.

27. The apparatus of claim 2 or 16, which includes a floatation nozzle disposed between each liquid seal and blowoff nozzle for directing a stream of air, under pressure, angularly against the traveling web at an angle substantially less than 90° to the plane of the web, the floatation nozzles being high volume/low pressure nozzles compared to the blowoff nozzles which are low volume/high pressure nozzles compared to the floatation nozzles each of which includes; (i) an enclosed compartment having an inlet and elongated slot facing the traveling web, (ii) baffling in the compartment for directing a uniform stream of air from the slot, and (iii) a deflector adjacent the slot for directing the stream of air angularly against the traveling web in the direction of the chamber.

* * * * *